United States Patent
Hardtl et al.

[11] Patent Number: 5,972,296
[45] Date of Patent: Oct. 26, 1999

[54] OXYGEN SENSORS MADE OF ALKALINE-EARTH-DOPED LANTHANUM FERRITES AND METHOD OF USE THEREOF

[75] Inventors: Karl-Heinz Hardtl, Hagenbach; Ulrich Schonauer, Karlsruhe; Andreas Krug, Igersheim, all of Germany

[73] Assignee: Heraeus Electro-Nite International, N.V., Houthalen, Belgium

[21] Appl. No.: 09/049,012

[22] Filed: Mar. 27, 1998

Related U.S. Application Data

[63] Continuation of application No. 08/737,623, filed as application No. PCT/EP95/01755, May 9, 1995, Pat. No. 5,843,858.

[51] Int. Cl.⁶ .................................................. G01R 27/22
[52] U.S. Cl. .................... 422/83; 204/291; 204/421; 204/424; 422/94; 422/98; 422/90; 436/79; 436/84; 436/127; 436/136; 436/137; 338/34; 73/23.31; 73/31.05; 73/31.06; 73/34
[58] Field of Search ........................ 204/421, 291, 204/424; 422/83, 90, 94, 95, 96–98; 436/127, 136, 137, 79, 84; 338/34; 73/23.31, 31.06, 31.05; 427/226

[56] References Cited

U.S. PATENT DOCUMENTS

| | | | |
|---|---|---|---|
| 3,951,603 | 4/1976 | Obayashi et al. | 23/232 E |
| 4,454,954 | 6/1984 | Williams et al. | 338/34 |
| 4,988,970 | 1/1991 | Hafele et al. | 338/34 |
| 5,306,411 | 4/1994 | Mazanec et al. | 204/265 |
| 5,397,541 | 3/1995 | Post | 422/88 |
| 5,582,710 | 12/1996 | Mairesse et al. | 205/634 |

FOREIGN PATENT DOCUMENTS

| | | |
|---|---|---|
| 0055104 | 6/1982 | European Pat. Off. . |
| 3098557 | 4/1988 | Japan . |
| 1240845 | 9/1989 | Japan . |

OTHER PUBLICATIONS

Kong et al "Gas-sensing property and mechanism of $Ca_xLa_{1-x}FeO_3$ ceramics". Sensors and activators B30 (1996) 217–221.

Yan et al "Sensing characteristics of rare earth perovsleite oxides for alcohols". Jilen Daxue Ziran Kexue Xuebao (1991), (2) 52–6.

Lu et al. "New kind of humidity sensitive ceramic w/ linear property". Proc. Electron. Compon. Technol. Conf. (1991) 41st., 261–3.

*Primary Examiner*—Jeffrey Snay
*Assistant Examiner*—S. Carrillo
*Attorney, Agent, or Firm*—Antonelli, Terry, Stout & Kraus, LLP

[57] ABSTRACT

Oxygen sensor for measuring resistance as a function of oxygen partial pressure, made of alkaline-earth-doped perovskitic lanthanum ferrites with the general formula $$La_{1-x}Me_xFeO_{3-\delta}$$

where Me is one of alkaline earth metals, Mg, Ca, Sr, and Ba, x is a degree of doping of the lanthanum ferrites. The oxygen sensor oxygen deficit of anion is 6=0 to 0.25, and the degree of doping of the lanthanum ferrites is x=0.1 to 0.3 and is selected to provide a temperature independent resistance property to the oxygen sensor in a lean range.

11 Claims, 8 Drawing Sheets

OXYGEN SENSORS MADE OF ALKALINE-EARTH-DOPED LANTHANUM FERRITES AND METHOD OF USE THEREOF

CROSS-REFERENCE TO RELATED APPLICATIONS

This application is a continuation application of Ser. No. 08/737,623, filed Mar. 3, 1997, now U.S. Pat. No. 5,843,858, which is a national stage application of PCT/EP95/01755, filed May 9, 1995.

FIELD OF THE INVENTION

The present invention relates to oxygen sensors according to the preamble of the main claim.

BACKGROUND OF THE INVENTION

Oxygen sensors that contain strontium ferrate, barium ferrate, or strontium-barium ferrate are known (U.S. Pat. No. 4,454,494). In these materials, the central iron atoms of the ferrate lattice are replaced by one to seventy atom-percent of an element from the group composed of titanium, cerium, tantalum, or niobium. The chemical stability limit of these materials is at a temperature of 850° C. with an $O_2$ partial pressure of $pO_2 = 10^{-18}$ bar, i.e. these materials decompose during prolonged operation in a reducing atmosphere, in a rich exhaust mixture for example.

The transition from p- to n- semiconducting sensor material in the materials of U.S. Pat. No. 4,454,494 takes place at a relatively high $O_2$ partial pressure ($>10^{-10}$ bar). This results in ambiguity of the sensor signal or insufficient signal at a gas change between rich and lean exhaust. In addition, the materials exhibit a clearly different temperature dependence for different $O_2$ partial pressure ranges.

An oxygen sensor is known (Chem. Abstr. 112 (1990), reference number 126, 210t) whose sensor material consists of an alkaline-earth-doped lanthanum ferrite. However, this sensor material is not used to measure the change in resistance based on the recorded oxygen partial pressure, but the thermo electric force. In these sensor materials, a significant temperature dependence prevails. To compensate for this temperature dependence, additional measures must be adopted, temperature-regulating measures or precise settings of currents and/or voltages for example. This document therefore contains technical prejudice against oxygen sensors that use the resistive properties of the sensor material. The thermo electromotive force is measured instead.

BRIEF SUMMARY OF THE INVENTION

The goal of the present invention is to provide improved sensor materials for oxygen sensors that are suitable for applications in lambda sensors for exhaust from combustion processes. In particular, these materials should exhibit a temperature-independent sensor resistance in the range of lean exhaust mixtures ($\lambda > 1$), while in the rich area they are temperature-activated in such fashion that the influence of the temperature on the sensor resistance can be compensated to the greatest degree possible by the temperature dependence of the thermodynamic equilibrium reactions of the gas components typically contained in the exhaust. As a result, the influence of temperature on the fluctuation and resistance between rich and lean ranges can be largely eliminated.

This goal is achieved by oxygen sensors made of alkaline-earth-doped perovskitic lanthanum ferrites according to the characterizing clause of the main claim.

DETAILED DESCRIPTION OF THE INVENTION

Figure 1:
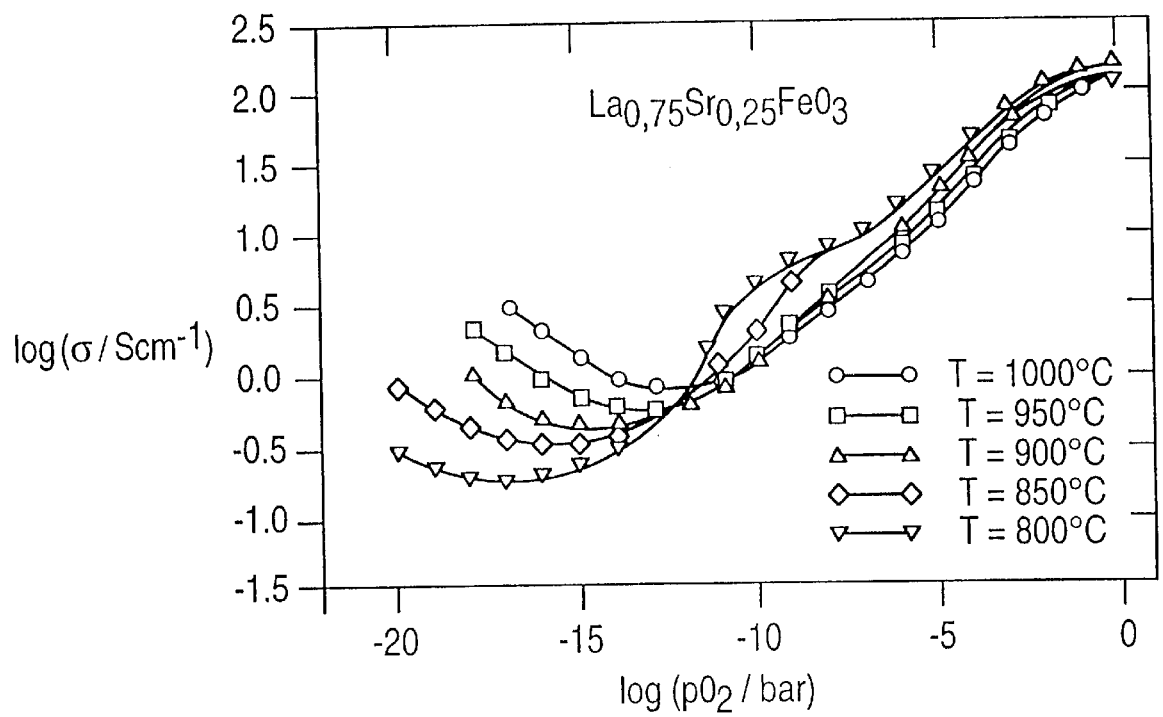
FIGS. 1 and 2 show measurement results with ferrite ceramics of the formula $La_{0.75}Sr_{0.25}FeO_3$ and $La_{0.5}Sr_{0.5}FeO_3$.

The alkaline-earth-doped lanthanum ferrites used in the oxygen sensors according to the invention have the general formula $$La_{1-x}Me_xFeO_{3-\delta}$$

where Me is one of the alkaline-earth metals Mg, Ca, Sr, and Br, especially Ca, Sr, and Ba, and the degree of doping x=0.1 to 0.3. The oxygen deficit of the anion is $\delta$=0 to 0.25.

It has been found that the material properties in such alkaline-earth-doped lanthanum ferrites can be significantly improved by a careful choice of the mixed-ceramic composition, i.e. by varying the ratio of lanthanum to alkaline earth. With a degree of doping in the range from 0.1 to 0.3, the ferrites exhibit a sensor characteristic that is independent of temperature and $pO_2$, provided the oxygen partial pressure remains in the range from $10^{-3}$ to $10^{-2}$ bar (lambda greater than 1). In the rich range (lambda less than 1) these materials exhibit an increased dependence on oxygen partial pressure and temperature. This influence of temperature on resistance however is largely compensated by the temperature dependence of the oxygen partial pressure that is produced by the thermodynamic equilibrium reactions of the exhaust components. This results in an approximately constant temperature-dependent sensor resistance in the range of rich exhaust mixtures.

This result is surprising, since U.S. Pat. No. 4,454,494 states that increased lanthanum doping of calcium ferrates results in an electrical conductivity that is too high and that these materials exhibit a pronounced hysteresis of conductivity as a function of temperature.

The alkaline-earth-doped La ferrites used are produced for example from $La_2O_3$, $Fe_2O_3$, and alkaline earth carbonate, with the starting materials being mixed, calcined, and sintered. The solid body reaction that proceeds at calcination temperature $T_K$ is described by the following chemical equation:

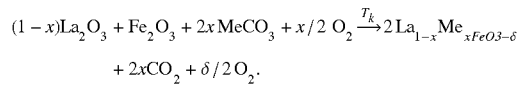

During this calcination reaction of the starting powder according to the above reaction equation, in addition to emission of $CO_2$, there is also an emission of small quantities of oxygen that results in an oxygen deficit $\delta$ in both the calcinate and in the mixed ceramic obtained from it. The $\delta$ in the starting powder is determined gravimetrically and varies for example as a function of the Sr content between $0.00 \leq \delta \leq 0.25$. The table below provides an overview of the oxygen deficits determined at room temperature as a function of the Sr content according to the formula $$La_{1-x}Sr_xFeO_{3-\delta}$$

| Sr Content/x | $\delta$ = oxygen defictic |
|---|---|
| 0.00 | 0.000 |
| 0.01 | 0.000 |
| 0.03 | 0.01 |
| 0.05 | 0.02 |
| 0.10 | 0.03 |
| 0.25 | 0.05 |
| 0.30 | 0.08 |
| 0.40 | 0.10 |
| 0.50 | 0.12 |

Measurements of electrical conductivity on bulk material indicate that $\delta$ for Sr contents below x=0.25 at temperatures up to 1000° C. and $pO_2$=1 bar changes only insignificantly. For mixed ceramics with an Sr content of x=0.3 or more, additional oxygen emission takes place above approximately T=600° C. ($pO_2$=1 bar), increasing with Sr content. For $La_{0.50}Sr_{0.40}FeO_3$ for example, for T=1000° C. and $pO_2$=1 bar, by means of thermogravimetry, a "basic" deficit evident from the above table at room temperature, an additional oxygen deficit of approximately 0.05 was found. This means that for $La_{0.60}Sr_{0.40}FeO_3$, at 1000° C. and $pO_2$=1 bar, one obtains a "total" $\delta$ of approximately $\delta$=0.15.

The $\delta$ range of the ferrites obtained extends from 0.00 to x/2 (x=0–25 mol%) and depends on temperature, alkaline earth content, and $pO_2$.

The $La_2O_3$ used is preferably initially subjected to an upstream roasting process in which it is annealed at temperatures of about 700 to 1000° C. The $La_2O_3$ can then be weighed stoichiometrically in the hot state (200° C. to 300° C.) together with the other constituents. The raw powder thus obtained is then mixed by grinding. The mixing time can last several hours, three hours for example for strontium mixed ceramics. The materials are dried and presintered to the starting powder.

The starting powder thus obtained is ground and then dried. It can be subjected to a multistage compression process. The subsequent sintering is performed at temperatures from 1250 to 1450° C.

The La ferrite powder thus produced can be processed with basic material and/or diluent to form a paste and this paste can be applied using a thick film technique, for example by screen printing, dipping, spraying, or injection, to a preferably nonconducting metal oxide substrate, $Al_2O_3$. They are dried and stoved. Sensors can be made in a very simple fashion using these techniques. The sensor materials are applied using thick film technology to carrier and are then stoved and/or tempered.

Surprisingly, it has been found that when the sensor materials are applied using thick film techniques, the temperature dependence of the resistance by comparison to corresponding bulk material with the same composition is much less. This follows from a comparison of bulk material with corresponding material applied using thick film techniques according to the examples below, with the corresponding temperature-dependent curves being shown in FIG. 3.

The invention will now be described in greater detail with reference to the examples.

EXAMPLE 1
Production of Sr-doped La-ferrite

To produce strontium-doped La ferrites, a raw powder composed of $La_2O_3$, $Fe_2O_3$, and $SrCO_3$ was used. The most important powder properties are summarized in the table below:

| Powder | Purity | $d_{50}/\mu m$ |
|---|---|---|
| $La_2O_3$ | >99.98% | <7 μm |
| $Fe_2O_3$ | >99.86% | <15 μm |
| $SrCO_3$ | >99.88% | 2–10 μm |

The average particle size diameter is in the range of $d_{50}$=2 μm–15 μm for all powders.

Each stoichiometric weighing of the various constituents is preceded by an annealing process for the $La_2O_3$ prior to preparation. Approximately 30 grams of $La_2O_3$ is heated at 5° C. per minute to T=830° C. and annealed at this temperature for at least five hours. Cooling then takes place at 1° C./min in general.

$La_2O_3$ is weighed stoichiometrically in the hot state (200° C.–300° C.) together with the remaining constituents. Approximately 50 grams of raw powder is mixed in a planetary ball mill with 50 balls (diameter=10 mm) in 150 ml $C_6H_{12}$ for three hours. After the mixed raw substances have dried (minimum twelve hours), they are presintered to the starting powder at T=1230° C. in air. The calcination time is ten hours. The heating rate is 10° C. per minute and the cooling rate follows the furnace time constant.

The starting powder is likewise ground for two hours in the planetary ball mill together with 150 ml of $C_6H_{12}$ and ten balls (diameter=20 mm) (average grain size $d_{50}$=4–5 μm) and then dried again for at least twelve hours. All of the powders exhibit a single-phase composition as determined by x-ray diffractometry.

EXAMPLE 2
Sintering Ceramic Bulk Materials

Beginning with approximately 2.5 g of starting powder, initially in a two-stage compression process (uniaxial pre-compression at 4 MPa, cold isostatic redensification with 220 MPa), green bodies with a green density of approximately 60% to 64% of the theoretical density are pressed. The sintering itself takes place at T=1400° C. ($t_s$=3 h), primarily in air at a heating rate of 10° C. per minute and a cooling rate of 5° C. per minute.

The sintering densities that can be reached with a preparation are in a range between 97% and 100% of the theoretically determined density. The maximum foreign phase component found is less than 1%.

Determination of $O_2$ Partial Pressure and Temperature Dependence

To perform the measurements of the specific electrical conductivity, parallelipipedal samples of various geometries were produced from the ceramic bulk material.

The contacts on the samples were obtained using the four-point method with platinum paste stoved for 1200° C. for twenty minutes.

Tests performed at room temperature using impedance spectroscopy show a purely ohmic electrical behavior for all ceramics.

The various ceramics were studied using a special sample carrier in a tubular furnace sealed gas-tight. The temperatures vary between 800° C. and 1000° C. and the $pO_2$ pressure can be set between $10^{-20}$ bar and $10^0$ bar.

For measuring the specific electrical resistance, initially the temperature equilibrium must be established in the measuring chamber. After setting the respective pO$_2$ pressure, the electrical resistance of the sample is determined within a fixed period of time (one to four hours).

Figure 2:
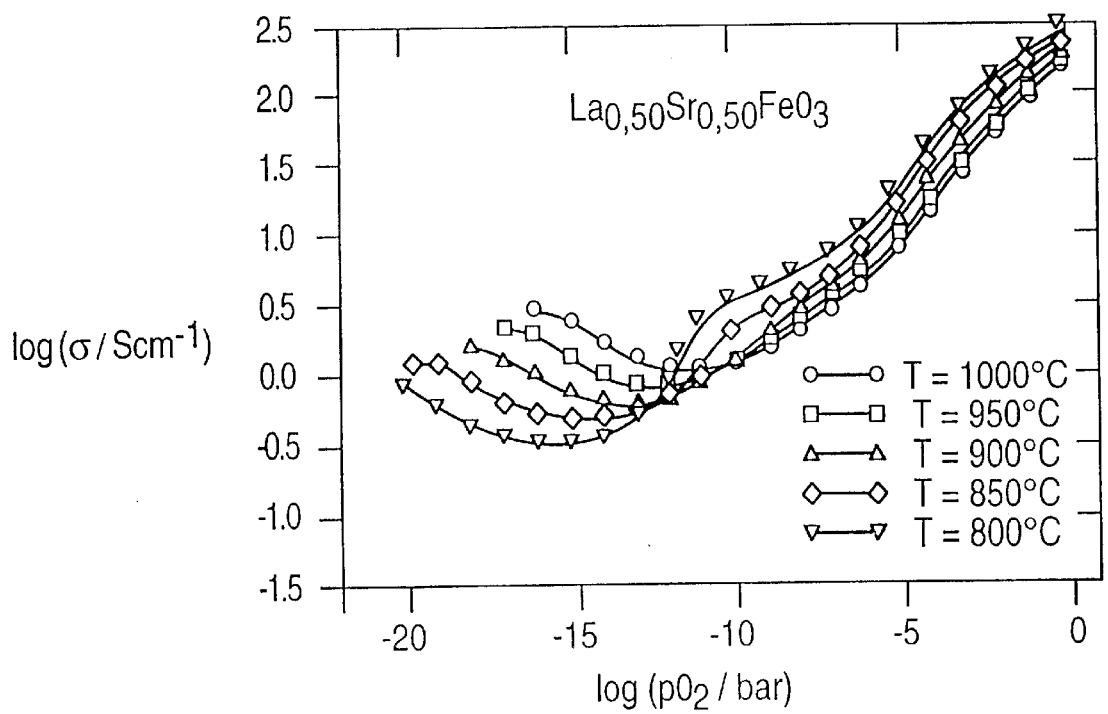

The measurement results with ferrite ceramics with the formulas La$_{0.75}$Sr$_{0.25}$FeO$_3$ and La$_{0.5}$Sr$_{0.5}$FeO$_3$ are shown in FIGS. 1 and 2. While at Sr dopings greater than 30% a pronounced temperature dependence is still observed in the range of high partial pressure (>10$^{-3}$ bar, lean mixture), this temperature dependence is negligible for dopings below 30%.

Figure 4:
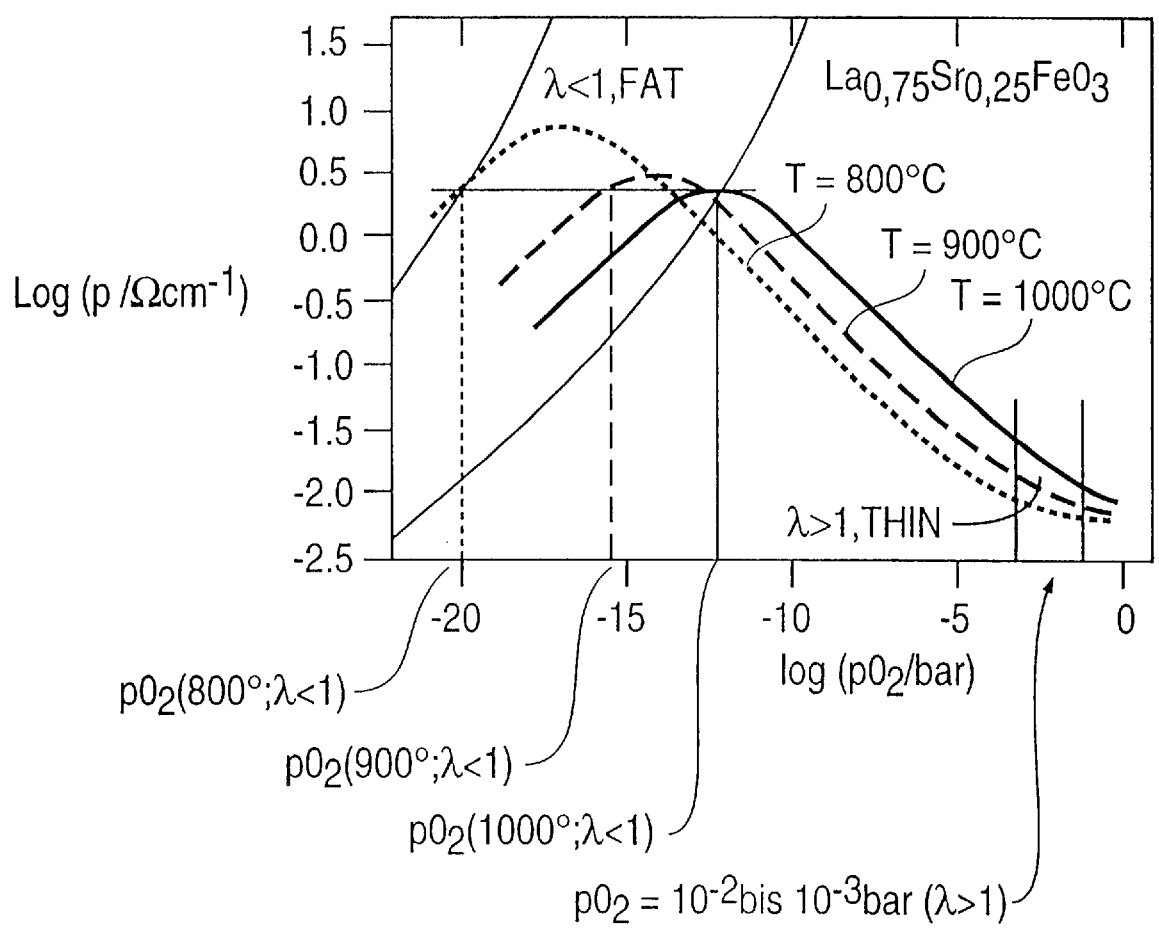
FIG. 4 shows the dependence of specific resistance log (P $\Omega m^{-1}$) on $O_2$ partial pressure at temperatures of 800°, 900° and 1000° C.
Figure 5:
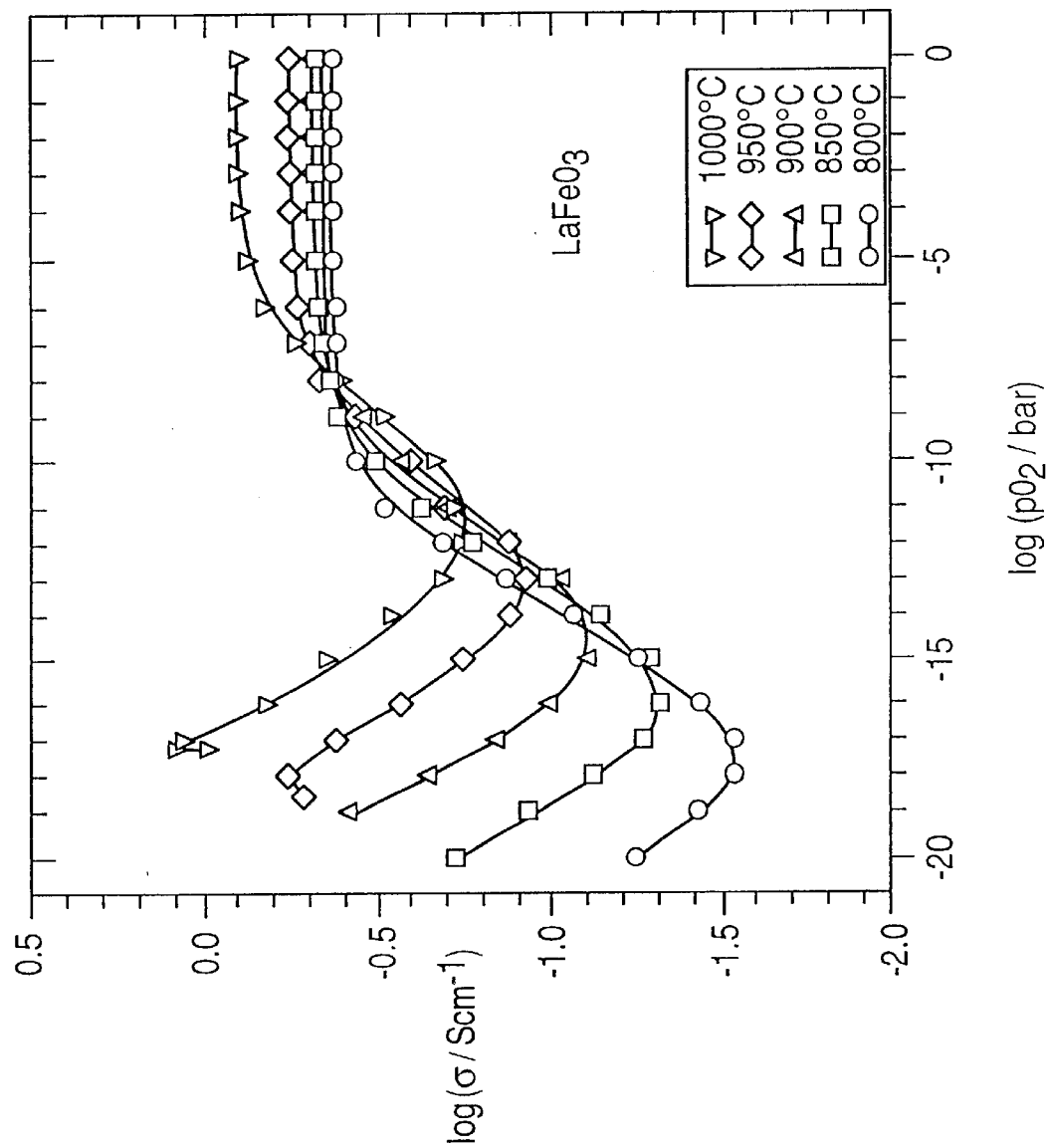
FIGS. 5–8 show additional graphs of specific electrical conductivity (sigma) as a function of temperature and oxygen partial pressure for various doped lanthanum products.
Figure 6:
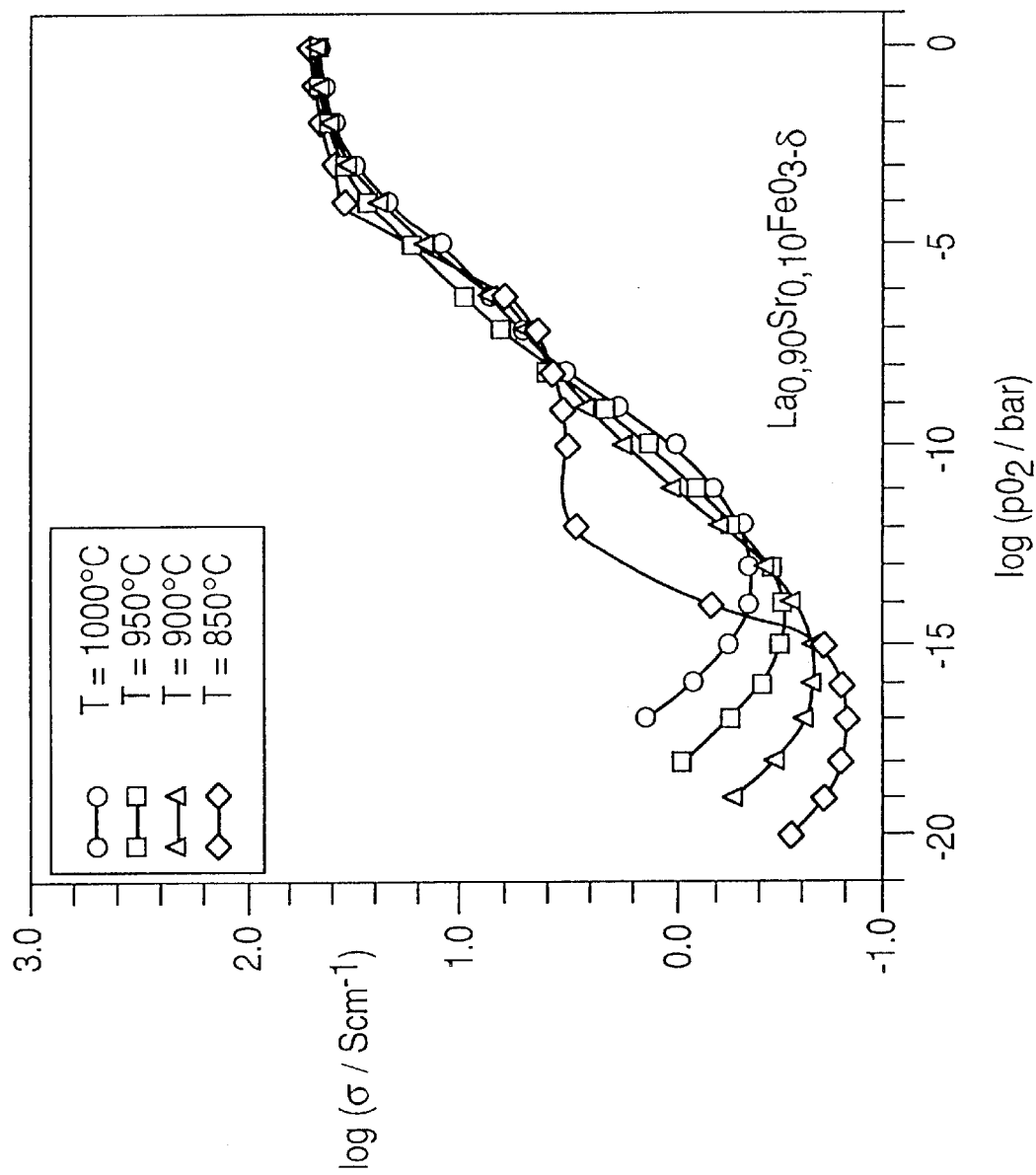
Figure 7:
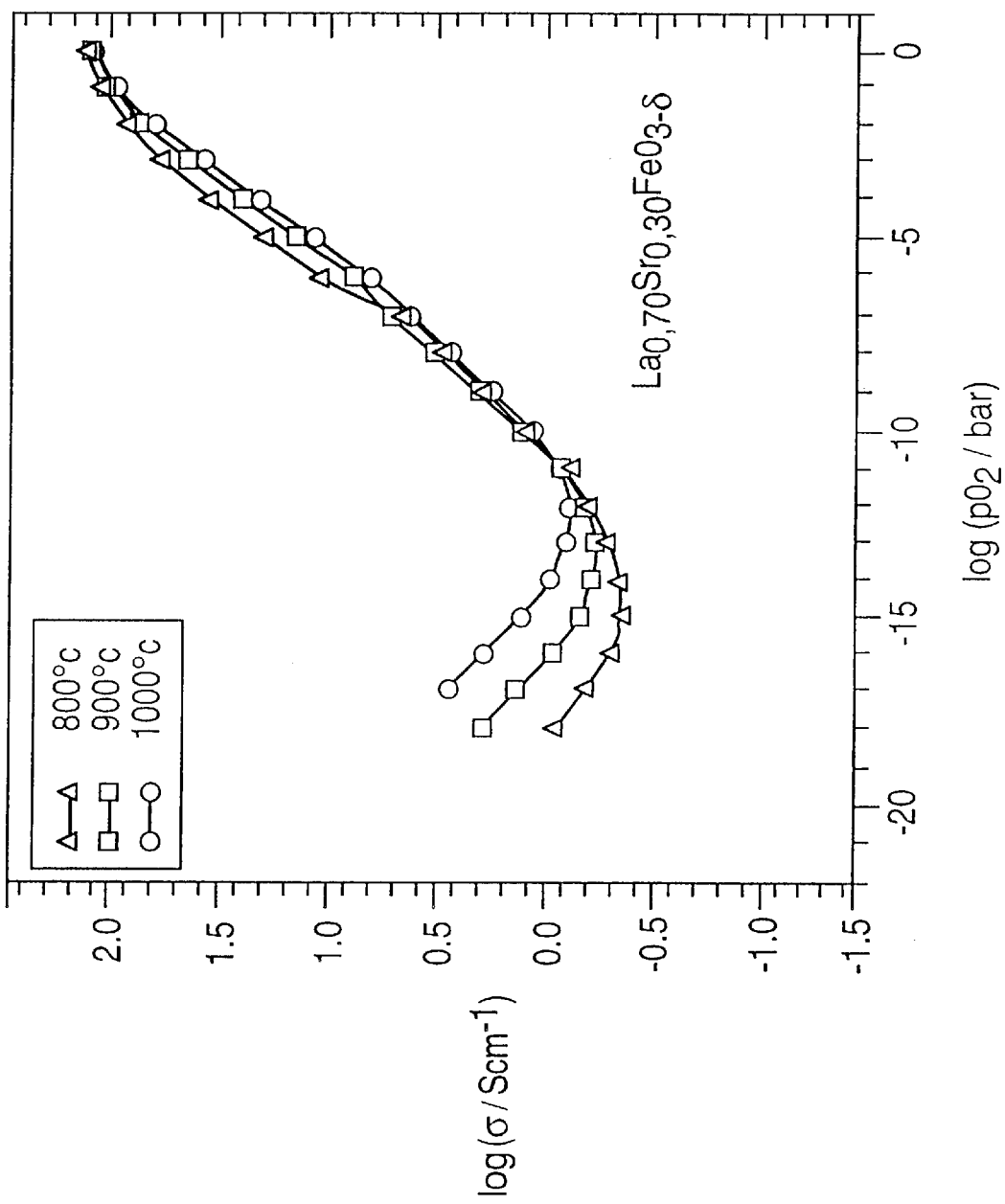
Figure 8:
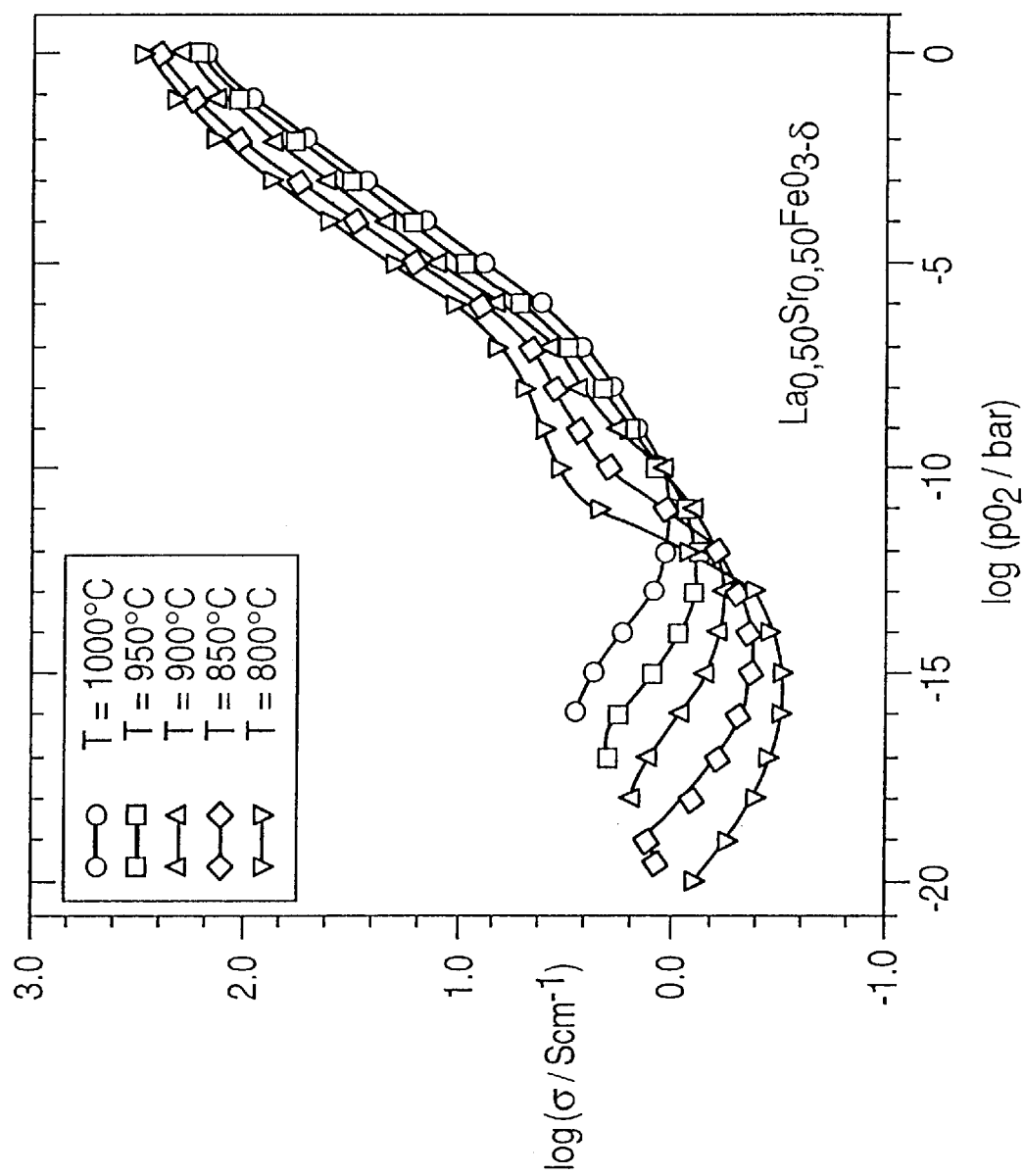
Figure 9:
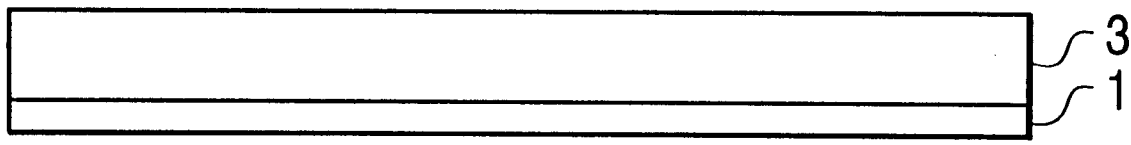
FIG. 9 shows, an oxygen sensor in accordance with the present invention, including non-conducting metal oxide substrate 1, thick film of alkaline-earth-doped perovskitic lanthanum ferrites 3, which includes contacts for measuring resistance.

FIG. 4 shows the dependence of specific resistance log (P/Ωm$^{-1}$) on O$_2$ partial pressure at temperatures of 800°, 900°, and 1000° C. The signals in the rich and lean areas differ sharply, but are relatively constant in one of the respective ranges.

For comparison, additional graphs of specific electrical conductivity (sigma) as a function of temperature and oxygen partial pressure for various doped lanthanum products are shown in FIGS. 5 to 8. The nondoped lanthanum ferrite, especially in the left branches of the curve, exhibits a pronounced temperature dependence, while with a doping degree of only 0.1 (with a variation at low temperature) the various temperature curves are nearly coincident. This is also the case with a degree of doping of 0.3 while with a higher degree of doping (0.5) the temperature dependence becomes stronger once again as can be seen from the fact that the curves no longer coincide.

EXAMPLE 3

Production of Ceramic Thick Films

The La ferrite powders produced according to Example 1 are processed with basic paste and/or diluent to form a paste and this paste is applied by screen printing to a nonconducting metal oxide substrate made of Al$_2$O$_3$, dried for fifteen minutes at 120° C., and stoved to the underlying sintered profile.

Increase at 20 K/min to 350° C.

Hold for 10 minutes at 350° C.

Increase at 20 K/min to 1200° C.

Hold for 25 minutes

Cool at 20 K/min to ambient temperature

Figure 3:
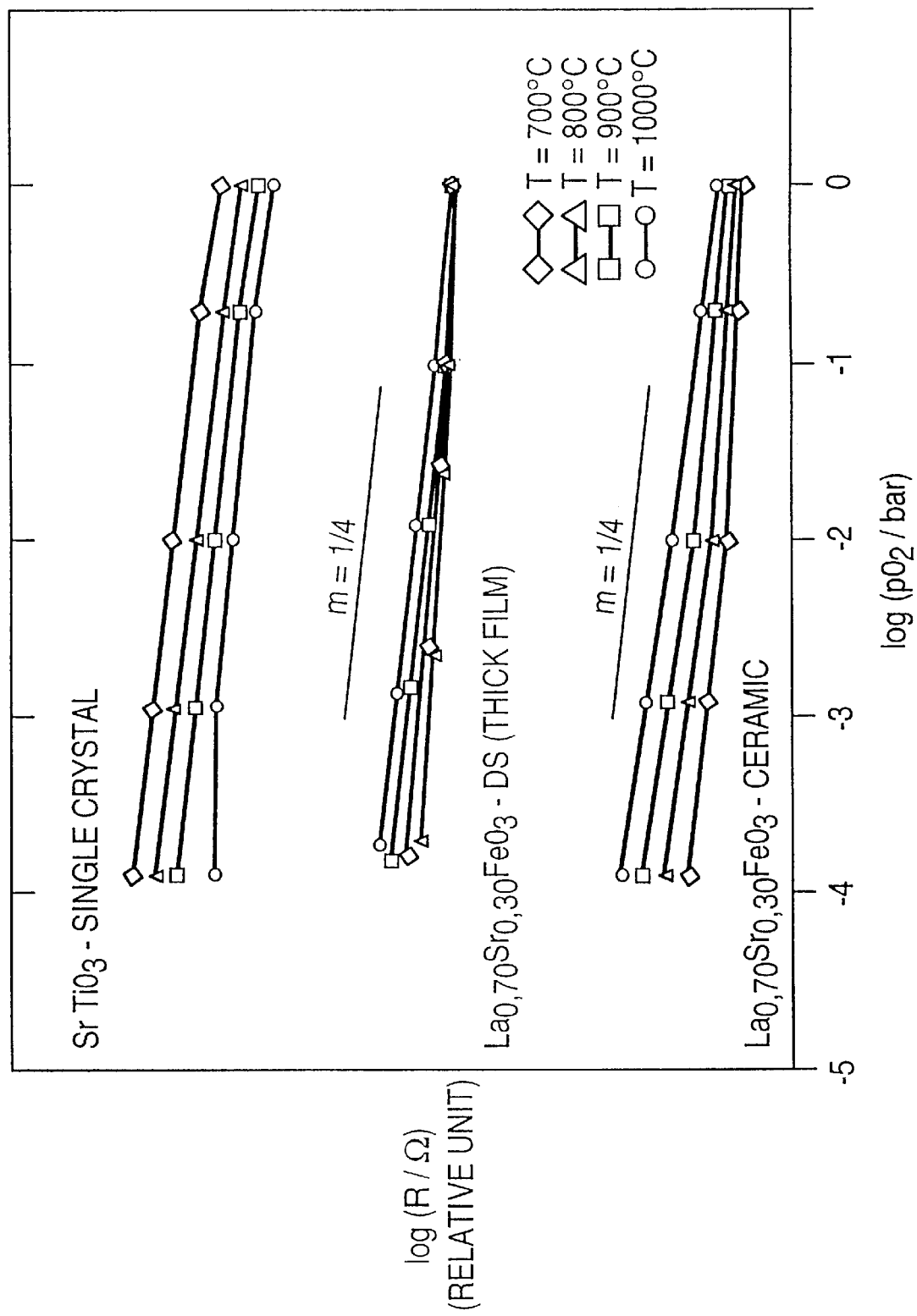
FIG. 3 shows that in the range of high partial pressures greater than $10^{-4}$ bar, in a comparison between ceramic bulk material according to FIG. 2 and a thick film according to Example 3, there is a clear reduction of the temperature dependence.

As shown in FIG. 3, in the range of high partial pressures greater than 10$^{-4}$ bar, in a comparison between ceramic bulk material according to FIG. 2 and a thick film according to example 3, there is once again a clear reduction of the temperature dependence, which is slight to begin with. This result is extremely surprising and could not be foreseen by the individual skilled in the art, since normally at best the same temperature effects are obtained for thick films and ceramics. In most cases, when thick film technology is employed, there is a worse ratio relative to temperature dependence and the characteristic curve by comparison with ceramic bulk material.

We claim:

1. A method of use of an oxygen sensor for measuring resistance as a function of oxygen partial pressure, wherein said oxygen sensor is made of alkaline-earth-doped perovskitic lanthanum ferrites with the general formula $$La_{1-x}Me_xFeO_{3-\delta}$$

where Me is one of Mg, Ca, Sr, and Ba, x is a degree of doping of the lanthanum ferrites, an oxygen deficit of anion δ=0 to 0.25, and the degree of doping of the lanthanum ferrites is x=0.1 to 0.3, and said alkaline-earth-doped perovskitic lanthanum ferrites are selected to provide a temperature independent resistance property to the oxygen sensor in a lean range, of gas components in exhaust, and said sensor includes contacts for measuring resistance, wherein said sensor is used as a lambda sensor to determine an air/fuel ratio in exhaust from a combustion process, comprising the step of providing said oxygen sensor in a combustion process, measuring resistance of said oxygen sensor and determining the air/fuel ratio in exhaust from said combustion process based on the measured resistance.

2. The method of use of an oxygen sensor for measuring resistance as a function of oxygen partial pressure, according to claim 1, wherein said alkaline-earth-doped perovskite lanthanum ferrites are applied as a thick film to a non-conducting metal oxide substrate.

3. An oxygen sensor for measuring resistance as a function of oxygen partial pressure, wherein said oxygen sensor is made of alkaline-earth-doped perovskitic lanthanum ferrites with the general formula $$La_{1-x}Me_xFeO_{3-\delta}$$

where Me is one of Mg, Ca, Sr, and Ba, x is a degree of doping of the lanthanum ferrites, an oxygen deficit of anion δ=0 to 0.25, and a degree of doping of the lanthanum ferrites is x=0.1 to 0.3, said sensor comprising a non-conducting metal oxide substrates, wherein said alkaline-earth-doped perovskitic lanthanum ferrites are applied as a thick film to said non-conducting metal oxide substrate, and contacts are positioned on said thick film of said alkaline-earth-doped perovskitic lanthanum ferrites for measuring resistance as a function of oxygen partial pressure, said oxygen sensor produced by a process comprising the steps of:

applying said alkaline-earth-doped perovskitic lanthanum ferrites to said substrate using thick film technology and stoving or tempering; or stoving and tempering said alkaline-earth-doped perovskitic lanthanum ferrites applied to said substrate.

4. A method of using an oxygen sensor for measuring resistance as a function of oxygen partial pressure, said oxygen sensor comprising a lamba sensor for determining an air/fuel ratio in exhaust from combustion processes, comprising the steps of:

providing, in a combustion process, an oxygen sensor made of alkaline-earth-doped perovskitic lanthanum ferrites with the general formula:

$$La_{1-x}Me_xFeO_{3-\delta}$$

where Me is one of the alkaline earth metals, Mg, Ca, Sr, and Ba, X is a degree of doping of the lanthanum ferrites, an oxygen deficit of anion δ=0 to 0.25, and the degree of doping of the lanthanum ferrites is x=0.1 to 0.3 and said alkaline-earth-doped perovskitic lanthanum ferrites are selected to provide a temperature independent resistance property to the oxygen sensor in a lean range, measuring resistance of said oxygen sensor and determining the air/fuel ratio in exhaust from said combustion process based on the measured resistance.

5. An oxygen sensor comprising alkaline-earth-doped perovskitic lanthanum ferrites with the general formula $$La_{1-x}Me_xFeO_{3-\delta}$$

where Me is selected from the group consisting of Mg, Ca, Sr, and Ba, and x is a degree of doping of the lanthanum ferrites, and an oxygen deficit of anion δ=0 to 0.25, characterized in that the degree of doping of the lanthanum ferrites is x=0.1 to 0.3, said sensor comprising a non-conducting metal oxide substrate, wherein said alkalineearth-doped perovskitic lanthanum ferrites are applied as a thick film to said non-conducting metal oxide substrate, and contacts are positioned on said thick film of said alkaline-earth-doped perovskitic lanthanum ferrites for measuring resistance as a function of oxygen partial pressure.

6. An oxygen sensor for measuring resistance as a function of oxygen partial pressure, wherein said oxygen sensor is made of alkaline-earth-doped perovskitic lanthanum ferrites with the general formula $$La_{1-x}Me_xFeO_{3-\delta}$$

where Me is one of Mg, Ca, Sr, and Ba, X is a degree of doping of the alkaline-earth-doped perovskitic lanthanum ferrites, an oxygen deficit of anion $\delta=0$ to 0.25, and the degree of doping of the alkaline-earth-doped perovskitic lanthanum ferrites is x=0.1 to 0.3 and said alkaline-earth-doped perovskitic lanthanum ferrites are selected to provide a temperature independent resistance property to the oxygen sensor in a lean range of gas components present in exhaust, said sensor comprising a non-conducting metal oxide substrate, wherein said alkaline-earth-doped perovskitic lanthanum ferrites are applied as a thick film to said non-conducting metal oxide substrate, and contacts are positioned on said thick film of said alkaline-earth-doped perovskitic lanthanum ferrites for measuring resistance as a function of oxygen partial pressure.

7. The oxygen sensor according to claim 6, wherein the oxygen sensor exhibit a temperature-independent sensor resistance in a lean range (lambda>1) and is temperature-activated in a rich range (lambda<1), wherein the influence of temperature on said sensor resistance is compensated by temperature dependence of thermodynamic equilibrium reactions of gas components contained in the exhaust in the rich range.

8. The oxygen sensor according to claim 6, wherein the degree of doping x=0.1 to 0.25.

9. The oxygen sensor according to claim 6, wherein the degree of doping is x=0.1 to 0.2.

10. The oxygen sensor according to claim 6, wherein said oxygen sensor has an oxygen partial pressure greater than $10^{-4}$ bar.

11. An oxygen sensor for measuring resistance as a function of oxygen partial pressure, said sensor made of a alkaline-earth-doped perovskite lanthanum ferrites with the general formula $$La_{1-x}Me_xFeO_{3-\delta}$$

where Me is one of the alkaline earth metals, Mg, Ca, Sr, and Ba, x is a degree of doping, the oxygen deficit if anion $\delta=0$ to 0.25, and the degree of doping of the lanthanum ferrites is x=0.1 to 0.3, wherein said alkaline-earth-doped perovskitic lanthanum ferrites are selected to provide a temperature independent resistance property to the oxygen sensor in a lean range, said sensor comprising a non-conducting metal oxide substrate, wherein said alkaline-earth-doped perovskitic lanthanum ferrites are applied as a thick film to said non-conducting metal oxide substrate, and contacts are positioned in said thick film of said alkaline-earth-doped perovskitic lanthanum ferrites for measuring resistance as a function of oxygen partial pressure, and wherein said oxygen sensor is produced by a process comprising the steps of applying said alkaline-earth-doped perovskitic lanthanum ferrites, using thick film technology to said non-conducting metal oxide substrate, and drying said thick film on said non-conducting metal oxide substrate for 15 minutes at a first temperature of 120° C., increasing said first temperature at 20K/min to a second temperature of 350° C. and holding said second temperature for 10 minutes at 350° C.; increasing said second temperature at 20K/min to a third temperature of 1200° C. and holding said third temperature for 25 minutes at 1200° C., and cooling said thick film on said non-conducting metal oxide substrate at 20K/min to ambient temperature.

* * * * *